(12) United States Patent
Radermacher

(10) Patent No.: US 9,642,211 B2
(45) Date of Patent: May 2, 2017

(54) DETECTING A PRESENCE OF AN OPERATING DIMMER

(71) Applicant: PHILIPS LIGHTING HOLDING B.V., Eindhoven (NL)

(72) Inventor: Harald Josef Günther Radermacher, Aachen (DE)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 0 days.

(21) Appl. No.: 14/758,910

(22) PCT Filed: Dec. 24, 2013

(86) PCT No.: PCT/IB2013/061303
§ 371 (c)(1),
(2) Date: Jul. 1, 2015

(87) PCT Pub. No.: WO2014/106795
PCT Pub. Date: Jul. 10, 2014

(65) Prior Publication Data
US 2015/0342003 A1    Nov. 26, 2015

Related U.S. Application Data

(60) Provisional application No. 61/748,474, filed on Jan. 3, 2013.

(51) Int. Cl.
*G01R 31/44* (2006.01)
*H05B 33/08* (2006.01)
(Continued)

(52) U.S. Cl.
CPC ....... *H05B 33/0884* (2013.01); *G01N 27/028* (2013.01); *G01R 31/44* (2013.01);
(Continued)

(58) Field of Classification Search
CPC H05B 33/0815; H05B 33/0845; H05B 37/02; H05B 33/0851; H05B 39/044;
(Continued)

(56) References Cited

U.S. PATENT DOCUMENTS 8,258,706 B2 * 9/2012 Maruyama ......... H05B 33/0803
                                                 315/119
8,710,766 B2 * 4/2014 Kanamori .......... H05B 33/0815
                                                 315/224
(Continued)

FOREIGN PATENT DOCUMENTS

EP    2456285 A1    5/2012

*Primary Examiner* — Vinh Nguyen

(57) ABSTRACT

A detection circuit is configured to detect the presence of an operating dimmer arranged to dim a lamp. The detection circuit includes a first circuit for measuring at a first frequency an impedance at a coupling arranged to carry a possibly dimmed feeding signal for the lamp. The first frequency is higher than the mains frequency of the mains which supplies the possibly dimmed feeding signal for the lamp. The first circuit provides a first output signal indicating the measured impedance at the first frequency. The detection circuit also includes a second circuit for analyzing the first output signal and providing a second output signal indicating whether the operating dimmer is present. The second output signal indicates that the operating dimmer is present if the measured impedance changes by at least a defined minimum deviation within a defined time interval.

19 Claims, 5 Drawing Sheets

(51) Int. Cl.
    *G01N 27/02*    (2006.01)
    *H05B 39/08*    (2006.01)
(52) U.S. Cl.
    CPC ......... *H05B 33/0815* (2013.01); *H05B 39/08* (2013.01); *H05B 33/0845* (2013.01)
(58) Field of Classification Search
    CPC  H05B 39/04; H05B 33/0803; H05B 33/0854; H05B 37/0281; H05B 41/3924; H05B 33/0842; H05B 33/0884; H05B 33/0824; H05B 33/089; H05B 39/041; H05B 41/14; H05B 41/36; H05B 41/38; H05B 41/3927; H01L 2924/12032; H01L 2924/12044; H02M 3/156; H02M 7/1557; H02M 7/217; H03K 17/74; G01R 31/44; G01R 19/175; G01R 31/024; G01R 31/2633
    See application file for complete search history.

(56)    References Cited

U.S. PATENT DOCUMENTS

| | | |
|---|---|---|
| 2011/0012530 A1 | 1/2011 | Zheng et al. |
| 2011/0025228 A1 | 2/2011 | Van Elk et al. |
| 2012/0212258 A1 | 8/2012 | Choi et al. |
| 2012/0217900 A1 | 8/2012 | Kanamori et al. |
| 2012/0286826 A1* | 11/2012 | King .................. H05B 33/0815 327/79 |

* cited by examiner

DETECTING A PRESENCE OF AN OPERATING DIMMER

CROSS-REFERENCE TO PRIOR APPLICATIONS

This application is the U.S. National Phase application under 35 U.S.C. §371 of International Application No. PCT/IB13/061303, filed on Dec. 24, 2013, which claims the benefit of U.S. Provisional Patent Application No. 61/748,474, filed on Jan. 3, 2013. These applications are hereby incorporated by reference herein.

FIELD OF THE INVENTION

The invention relates to a detection circuit for detecting a presence of an operating dimmer arranged to dim a lamp. The invention further relates to devices, and to a method.

Examples of such devices are lamps and filters and power converters comprising a detection circuit for detecting a presence of an operating dimmer or comprising an input for receiving information from the detection circuit.

BACKGROUND OF THE INVENTION

Existing detection circuits for detecting presences of operating dimmers arranged to dim lamps detect voltage levels between the mains and the lamps and base their decisions upon the detected voltage levels. These decisions are relatively unreliable.

SUMMARY OF THE INVENTION

It is an object of the invention to provide an improved detection circuit. Such an improved detection circuit makes relatively reliable decisions. Further objects of the invention are to provide improved devices, an improved lamp, an improved power converter, and an improved method.

According to a first aspect, a detection circuit is provided for detecting a presence of an operating dimmer arranged to dim a lamp, the detection circuit comprising a first circuit for measuring an impedance at a coupling arranged to carry a possibly dimmed feeding signal for the lamp and for providing a first output signal, the first output signal defining the measured impedance, the measured impedance comprising an impedance at a frequency larger than a mains frequency, and a second circuit for analyzing the first output signal and for providing a second output signal, the second output signal defining the operating dimmer being present or not.

One side of the coupling is for example coupled to the mains, possibly via a dimmer. The other side of the coupling is coupled to the lamp, possibly via a power converter or another unit. The coupling carries a dimmed feeding signal to the lamp when the dimmer is present and operating. The coupling carries a non-dimmed feeding signal to the lamp when the dimmer is present without dimming or when the dimmer is bridged or when a dimmer is not present. The first circuit determines the impedance at the coupling and provides the first output signal. The impedance is for example measured between the conductors of a two-conductor-coupling or between one conductor of a one-conductor-coupling and ground or between the terminals of the lamp, the power converter or the other unit, when being connected to the coupling etc. The measured impedance is the impedance at the frequency larger than the mains frequency. The first output signal defines this measured impedance in a more precise way or a less precise way and in an absolute way or a relative way etc. The second circuit analyses the first output signal and provides the second output signal. The second output signal defines the operating dimmer being present or not.

As a result, an improved detection circuit has been provided. Such an improved detection circuit makes relatively reliable decisions. These decisions are relatively reliable owing to the fact that the measured impedances have appeared to be more reliable values than the prior art voltage levels that are detected independently from a frequency value.

The impedance may be determined at one fixed frequency or at one variable frequency or at multiple frequencies, e.g. within a frequency band, at a basic frequency and its harmonics, etc.

An embodiment of the detection circuit is defined by the first circuit being arranged to measure the impedance several times per time-interval, at least one change in the measured impedance of a certain minimum deviation or more within the time-interval being indicative for the presence of the operating dimmer. The time-interval is for example half a cycle of the mains such as 10 msec at 50 Hz or 8.4 msec at 60 Hz or a full cycle or a multiple thereof etc. The certain minimum deviation is for example a certain minimum variation of a real average value or a certain minimum variation of a calculated average value or a certain minimum variation of another value etc. Preferably, at least two changes may be indicative for the presence of the operating dimmer, a first change from a first impedance value to a second impedance value, and a second change from the second impedance value to the first impedance value. During each transition, any value different from the first and second values may occur, but at the end of the transition, a setting will be reached.

An embodiment of the detection circuit is defined by the second circuit comprising
a filter for filtering the first output signal,
an averaging circuit for averaging the filtered first output signal,
a threshold circuit for in response to the averaged and filtered first output signal providing a threshold value,
a comparator for comparing the filtered first output signal with the threshold value, and
a controller for in response to a comparison result from the comparator producing the second output signal.

The filter filters (much) higher and/or (much) lower frequencies. The averaging circuit determines an average value of whatever kind. The threshold circuit provides a threshold value such as the average value minus the minimum variation or such as the average value plus the minimum variation respectively. The comparator compares the filtered first output signal with the threshold value, and informs the controller that a value of the filtered first output signal is respectively smaller or larger than the threshold value, or not. The controller processes this information and produces the second output signal.

An embodiment of the detection circuit is defined by the threshold value comprising first and second threshold values, the comparator being arranged to compare the filtered first output signal with the first and second threshold values, and the controller being arranged to produce the second output signal in response to first and second comparison results from the comparator. The threshold circuit provides a first threshold value such as the average value plus the minimum variation and provides a second threshold value such as the average value minus the minimum variation. The comparator compares the filtered first output signal with the threshold values, and informs the controller that a value of the filtered first output signal is larger than the first threshold value or smaller than the second threshold value, or in between. The controller processes this information and produces the second output signal.

An embodiment of the detection circuit is defined, wherein the controller is arranged to produce the second output signal further in response to the first output signal, the filtered first output signal and/or the averaged and filtered first output signal, and/or wherein the second output signal, in case of the operating dimmer being present, further defines one or more characteristics of the operating dimmer. Such characteristics may be leading edges and trailing edges to distinguish leading edge dimmers and trailing edge dimmers and may be identifications to identify dimmers etc. These characteristics may be derived from the way the measured impedance is changing (linearly, non-linearly, with a relatively steep slope, with a relatively non-steep slope, with an increasing change, with a decreasing change etc.).

For the above described embodiments, the impedance is for example measured by the first circuit comprising an impedance measurement unit. The impedance measurement unit will generate a voltage signal at said frequency and add it to the coupling and then detect a current signal at said frequency resulting from the voltage signal and then convert a detection result into the impedance, for example by dividing the voltage signal by the current signal. Alternatively, the impedance is for example measured by the first circuit comprising a filter and a detector, whereby the filter is filtering all other frequency components of the feeding (voltage) signal outside a selected range and the detector is detecting the frequency component of the feeding (voltage) signal in the selected range at said frequency larger than the mains frequency. The last case is based on the assumption that the operating dimmer is usually changing the feeding signal such that the impedance at many different frequencies is changed. A dedicated frequency or a range of frequencies is used for the determination, the other frequencies are to be filtered.

Such an impedance measurement unit may be relatively complex and relatively high cost, and a use of one out of many different frequency components created by an unknown and therefore unpredictable dimmer may sometimes not be an ideal solution. The following embodiments provide improved solutions thereto.

An embodiment of the detection circuit is defined by the first circuit comprising
a first input to be connected to said coupling,
a second input to be connected to a generator arranged to generate a signal at said frequency, and
an output for providing the first output signal or a filtered first output signal.

According to this embodiment, the signal at said frequency is generated and used for determining the impedance. In this case, the signal may be a voltage signal, and the (filtered) first output signal may be a (filtered) first output voltage signal. This (filtered) first output voltage signal represents the measured impedance and should not be confused with the voltage levels as detected in accordance with the prior art. These prior art detected voltage levels are not related to the measured impedance at said frequency larger than the mains frequency.

An embodiment of the detection circuit is defined by the first circuit further comprising:

a transformer, a first winding being coupled to the first input, a second winding being coupled to the second input, the second winding further being coupled to a network, the network being coupled to the output.

The transformer provides galvanic isolation and combines the high-frequency signal and the coupling such that the high-frequency impedance can be determined via (a part of) the network. In case galvanic isolation is not required, the transformer may be avoided.

Preferably, the detection circuit may further be defined by the first winding being coupled to terminals of the first input via a first capacitor, the second winding being coupled to terminals of the second input via a first serial connection of a first resistor, a second capacitor and a buffer, and the network comprising a second serial connection of a second resistor and a third capacitor, the second serial connection being coupled in parallel to the second winding, and terminals of the output being coupled in parallel to the third capacitor. This is a low cost and simple and robust embodiment that for example can be used for testing purposes.

An embodiment of the detection circuit is defined by the coupling being arranged to be connected to the lamp via a power converter. This embodiment does not need an additional generator but uses an existing power converter also known as switched mode power supply. The frequency larger than the mains frequency may for example be chosen equal to a switching frequency of the power converter.

An embodiment of the detection circuit is defined by a switching frequency of the power converter being an adaptable switching frequency for improving a quality of the first output signal and/or the second output signal. By adapting the switching frequency of the power converter, an influence of possibly present electromagnetic interference filters is reduced, owing to the fact that electromagnetic interference filters are usually designed to suppress one particular switching frequency. The impedance may be measured for one and the same frequency larger than the mains frequency or for different frequencies each larger than the mains frequency per time-interval.

An embodiment of the detection circuit is defined by a filter of the power converter being an adaptable filter for improving a quality of the first output signal and/or the second output signal. This way, an influence of the present filter can be reduced. The filter may be located inside or outside the power converter.

According to a second aspect, a device is provided comprising the detection circuit as defined above and further comprising a filter, a power converter and/or the lamp.

According to a third aspect, a device is provided comprising the detection circuit as defined above and further comprising the lamp that comprises at least one light emitting diode.

According to a fourth aspect, device is provided comprising an input for receiving the second output signal from the detection circuit as defined above. Via the second output signal, information is supplied from the detection circuit to the device for adjusting the device in response to the information.

According to an embodiment, the device is defined by further comprising a filter, a power converter and/or the lamp. Preferably, the filter, the power converter and/or the lamp can be adjusted in response to the second output signal.

According to a fifth aspect, a method is provided for detecting a presence of an operating dimmer arranged to dim a lamp, the method comprising the steps of
measuring an impedance at a coupling arranged to carry a possibly dimmed feeding signal for the lamp and providing a measurement result, the measurement result defining the measured impedance, the measured impedance comprising an impedance at a frequency larger than a mains frequency, and analyzing the first result and providing an analysis result, the analysis result defining the operating dimmer being present or not.

An insight is that a dimmer may be looked at as a parallel arrangement of a power part and a control part. The power part comprises a switch, being either "open" or "closed". In general, an amplitude of the possible current in the control part (for example 1 mA-100 mA) is significantly lower than an amplitude of the possible current in the power part (for example >1000 mA). In addition, the power part is designed for a low dropout voltage in order to minimize the losses in the dimmer. The control part is, in contrast, designed to carry a limited current while a significant voltage drop is preset across the dimmer terminal. In other words, the impedance of the power part may be (very) low or (very) high, whereas the impedance of the control part may be somewhere in between medium to (very) high. And the impedance of the dimmer is situated in series with the impedance of the mains.

A basic idea is that the detection circuit should measure an impedance between the mains (and a possible dimmer) on the one hand and the lamp on the other hand and should analyze a measurement result to find out whether an operating dimmer is present or not.

A problem to provide an improved detection circuit has been solved. A further advantage is that the detection results may be used to improve the operations of the lamps and/or of the power converters.

These and other aspects of the invention will be apparent from and elucidated with reference to the embodiments described hereinafter.

DETAILED DESCRIPTION OF EMBODIMENTS

Figure 1:
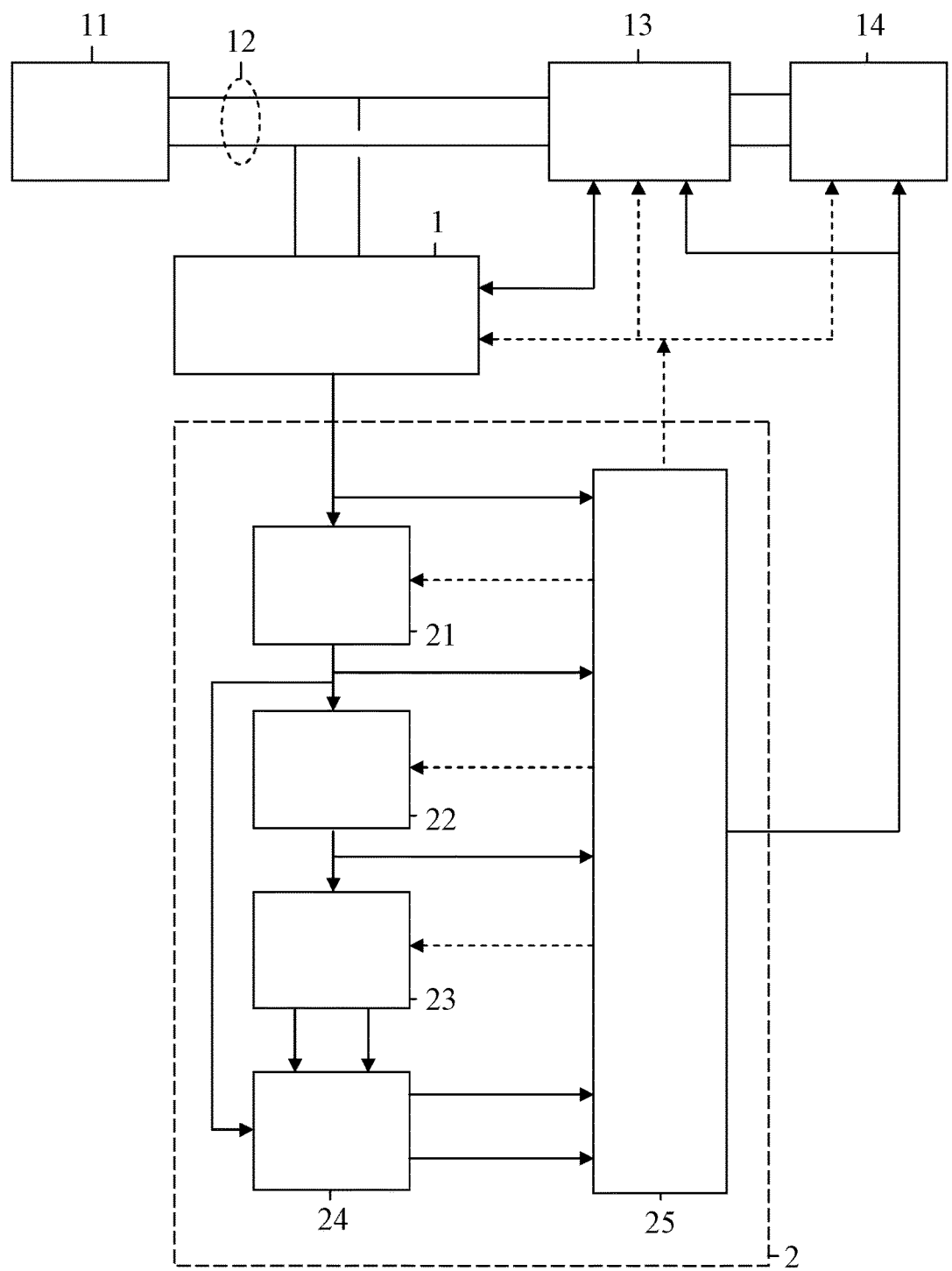
FIG. 1 shows an embodiment of a detection circuit comprising a first circuit and a second circuit.

In the FIG. 1, an embodiment of a detection circuit 1, 2 comprising a first circuit 1 and a second circuit 2 is shown. A coupling 12 here comprising two conductors is connected to a unit 11 representing the mains or a combination of the mains and a dimmer and via a power converter 13 to a lamp 14. Alternatively, the coupling 12 may comprise one conductor, with the other conductor being ground. Alternatively, the power converter 13 may be left out. However, in case the lamp 14 comprises one or more light emitting diodes of whatever kind and in whatever combination, the power converter 13 will usually be present.

The detection circuit 1, 2 comprises a first circuit 1 connected to the coupling for measuring an impedance at the coupling 12. The coupling 12 is arranged to carry a possibly dimmed feeding signal for the lamp 14. The first circuit 1 provides a first output signal to a second circuit 2. This first output signal defines the measured impedance. The second circuit 2 analyses the first output signal and provides a second output signal. This second output signal defines the operating dimmer being present or not.

The impedance is the impedance at the frequency larger than the mains frequency of 50 Hz or 60 Hz. This measured impedance is a parallel connection of an impedance of the unit 11 and an impedance of the unit 14 or 13+14, while excluding the impedance of the coupling 12 itself. In case the unit 11 comprises an operating dimmer, the impedance of the unit 11 will show relatively large changes, that can be measured via the first circuit 1.

The first circuit 1 measures the impedance several times per time-interval. At least one change in the high-frequency impedance of a certain minimum deviation or more within the time-interval will be indicative for the presence of the operating dimmer. This time-interval is for example half a cycle of the mains such as 10 msec at 50 Hz or 8.4 msec at 60 Hz or a full cycle or a multiple thereof etc. The certain minimum deviation is for example a certain minimum variation of a real average value or a certain minimum variation of a calculated average value or a certain minimum variation of another value etc.

The second circuit 2 comprises a filter 21 for filtering the first output signal, an averaging circuit 22 for averaging the filtered first output signal, and a threshold circuit 23 for in response to the averaged and filtered first output signal providing a threshold value. The second circuit 2 further comprises a comparator 24 for comparing the filtered first output signal with the threshold value, and a controller 25 for in response to a comparison result from the comparator 24 producing the second output signal. The filter 21 filters (much) higher and (much) lower frequencies. The averaging circuit 22 determines an average value of whatever kind. The threshold circuit 23 provides a threshold value such as the average value minus the minimum variation or such as the average value plus the minimum variation respectively. The comparator 24 compares the filtered first output signal with the threshold value, and informs the controller 25 that a value of the filtered first output signal is respectively smaller or larger than the threshold value, or not. The controller 25 processes this information and produces the second output signal.

Preferably, the threshold circuit 23 provides a first threshold value such as the average value plus the minimum variation and provides a second threshold value such as the average value minus the minimum variation. The comparator 24 compares the filtered first output signal with the threshold values, and informs the controller 25 that a value of the filtered first output signal is larger than the first threshold value or smaller than the second threshold value, or in between. The controller 25 processes this information and produces the second output signal.

Preferably, the controller 25 may, for producing the second output signal, use the first output signal and/or the filtered first output signal and/or the averaged and filtered first output signal. Further, the controller 25 may control the first circuit 1 for adapting the measurement, the filter 21 for adapting the filtering, the averaging circuit 22 for adapting the averaging, the threshold circuit 23 for adapting the threshold value(s), the power converter 13 for adapting a power converter feature and the lamp 14 for adapting a lamp feature. Yet further, the first circuit 1 and the power converter 13 may exchange information for adapting their functions. Finally, the second output signal may, in case of the operating dimmer being present, further define one or more characteristics of this operating dimmer. This second output signal may further be supplied to the power converter 13 for adapting the power converter feature or another feature and to the lamp 14 for adapting the lamp feature or another feature.

Figure 2:
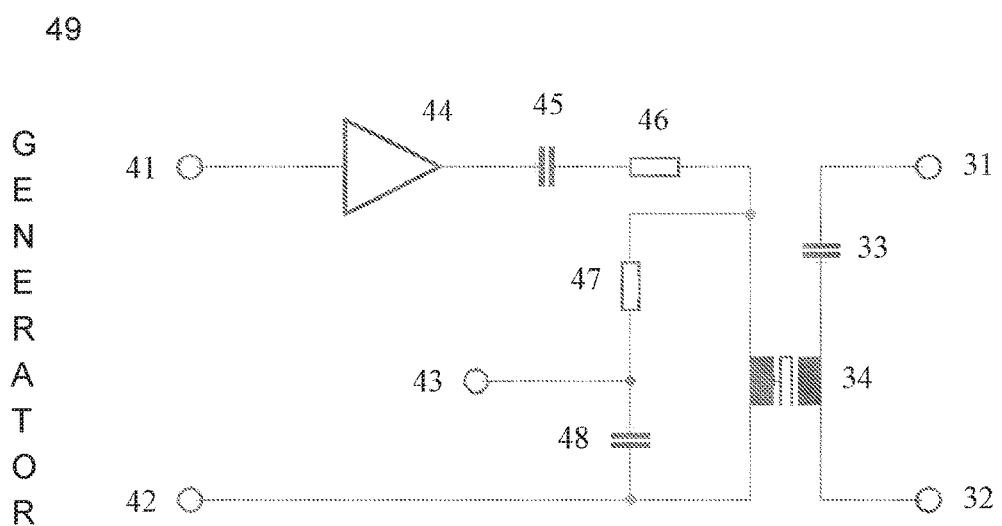
FIG. 2 shows an embodiment of a first circuit.

In the FIG. 2, an embodiment of a first circuit 1 is shown. 6. The first circuit 1 comprises a first input 31, 32 to be connected to said coupling 12, a second input 41, 42 to be connected to a generator 49 arranged to generate a signal at said frequency, and an output 43, 42 for providing the first output signal or a filtered first output signal. The first circuit 1 may further comprise a transformer 34. A first winding of the transformer 34 is coupled via a first capacitor 33 to the first input 31, 32. A second winding of the transformer 34 is coupled via a first serial connection of a first resistor 46, a second capacitor 45 and a buffer 44 to the second input 41, 42. The second winding is further coupled to a network 47, 48 comprising a second serial connection of a second resistor 47 and a third capacitor 48. The second serial connection is coupled in parallel to the second winding, and terminals of the output 43, 42 are coupled in parallel to the third capacitor 48.

In case the power converter 13 is present, instead of using the embodiment shown in the FIG. 2, the existing power converter 13 also known as switched mode power supply may be used for providing a signal at a frequency larger than the mains frequency. This frequency may for example be chosen equal to a switching frequency of the power converter 13. Preferably, the switching frequency of the power converter 13 may be an adaptable switching frequency for improving a quality of the first output signal and/or the second output signal. By adapting the switching frequency of the power converter 13, for example via a control signal from the controller 25 or via the first or second output signal, an influence of possibly present electromagnetic interference filters is reduced, owing to the fact that electromagnetic interference filters are usually designed to suppress one particular switching frequency. The impedance may be measured for one and the same frequency larger than the mains frequency or for different frequencies each larger than the mains frequency per time-interval.

Figure 3:
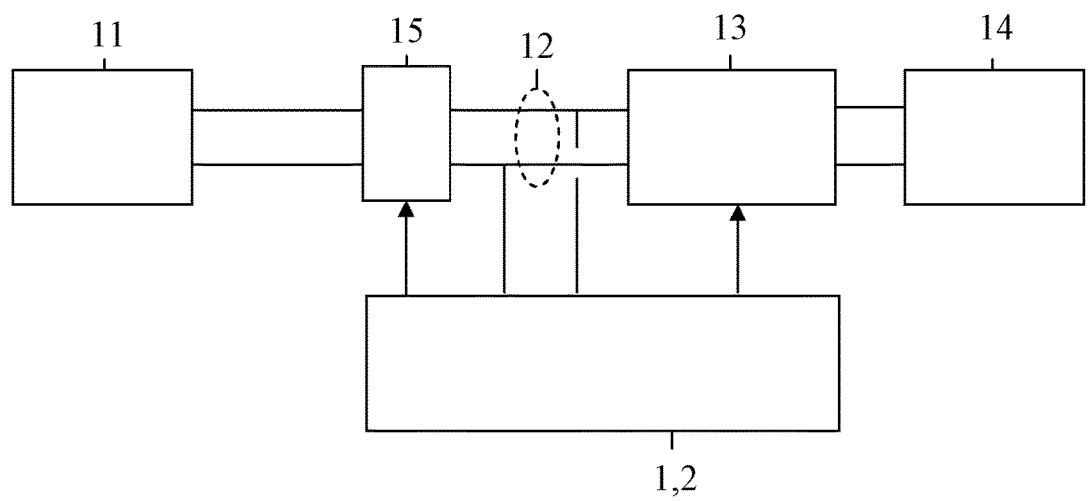
FIG. 3 shows the detection circuit in combination with a power converter and a filter.
Figure 4:
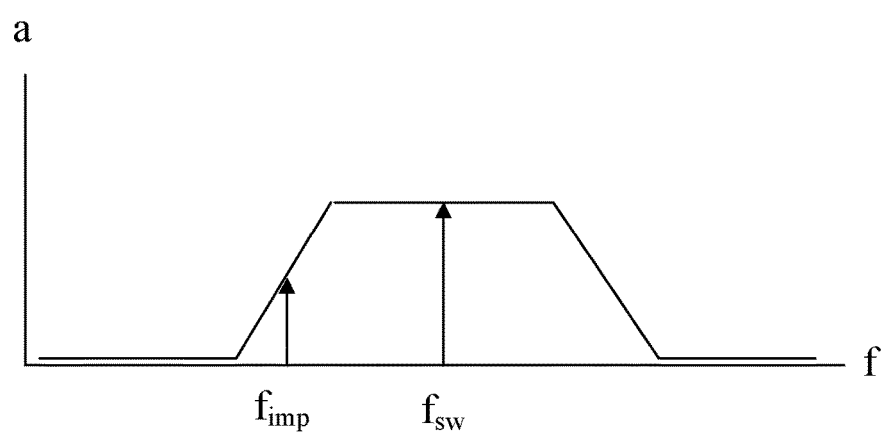
FIG. 4 shows an attenuation of the filter versus frequencies.

In the FIG. 3, the detection circuit 1, 2 in combination with a power converter 13 and a filter 15 is shown, and in the FIG. 4 an attenuation of the filter 15 versus frequency is shown. The detection circuit 1, 2 may control the power converter 13 to temporarily reduce the switching frequency $f_{sw}$ to the frequency $f_{imp}$ for which the impedance is to be measured, to reduce an influence of the filter 15, that at $f_{imp}$ has a smaller attenuation than at $f_{sw}$. The detection circuit 1, 2 may further control the filter 15 to temporarily reduce the attenuation at the frequency $f_{imp}$ for which the impedance is to be measured, to reduce an influence of the filter 15. This way, a quality of the first output signal and/or the second output signal can be improved.

Figure 5:
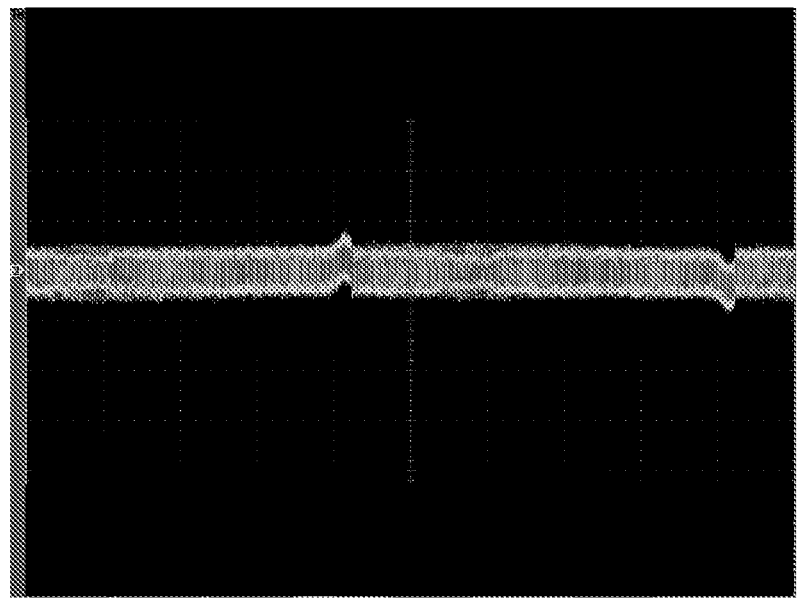
FIG. 5 shows an impedance value at a frequency, in case no dimmer is present.

In the FIG. 5, an impedance value at a frequency is shown, in case no dimmer is present, in the form of a signal amplitude of a (high-frequency) signal as captured via the first circuit 1 as shown in the FIG. 2 (vertical axis: signal amplitude, horizontal axis: time, total duration from left to right 20 msec.). The amplitude of the (high-frequency) signal is an indicator of the impedance. Based on component values chosen for the first circuit 1, such as the value of the first resistor 46, the signal amplitude can be translated into the impedance. The value of this impedance is stable, since the amplitude of the (high-frequency) signal is stable (the two low-frequency deviations in the plot are to be ignored in view of the (high-frequency) signal).

Figure 6:
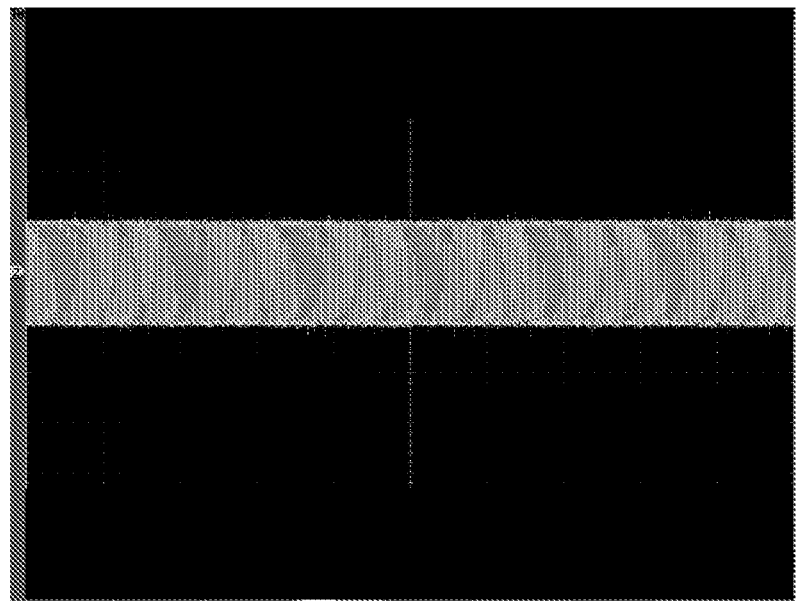
FIG. 6 shows an impedance value at a frequency, in case a dimmer is present but switched off.

In the FIG. 6, an impedance value at a frequency is shown, in case a dimmer is present but switched off (vertical axis: signal amplitude, horizontal axis: time, total duration from left to right 20 msec.).

Figure 7:
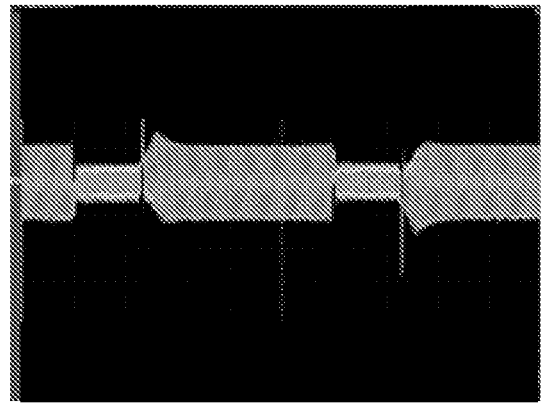
FIG. 7 shows an impedance value at a frequency, a value of the impedance changing owing to the fact that a first dimmer is present.

In the FIG. 7, an impedance value at a frequency is shown, a value of the impedance changing owing to the fact that a first dimmer is present (vertical axis: signal amplitude, horizontal axis: time, total duration from left to right 20 msec.).

Figure 8:
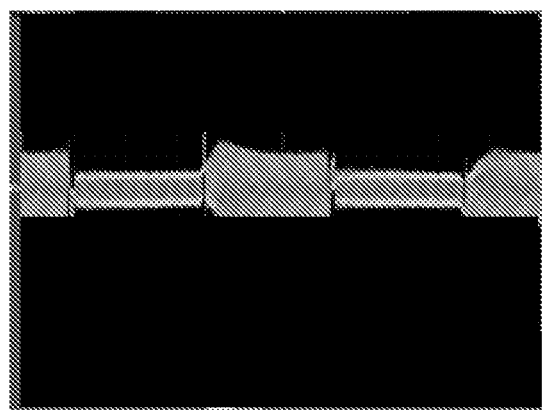
FIG. 8 shows an impedance value at a frequency, a value of the impedance changing owing to the fact that a second dimmer is present.

In the FIG. 8, an impedance value at a frequency is shown, a value of the impedance changing owing to the fact that a second dimmer is present (vertical axis: signal amplitude, horizontal axis: time, total duration from left to right 20 msec.).

Clearly, the impedances change during the mains cycles, i.e. within each half of a mains cycle there is at least one time-period, wherein the impedance value is lower than an average value and at least one time-period wherein the impedance value is higher than the average value. This will be analyzed by the second circuit 2.

Parts of the detection circuit 1, 2, such as (a part of) the first circuit 1 or (a part of) the second circuit 2, may be realized through hardware, software or a mixture of both. Further, each one of the circuits 1 and 2 may at least partly function in an analogue way, in a digital way, or in a mixture of both.

Summarizing, detection circuits 1, 2 for detecting presences of operating dimmers arranged to dim lamps 14 comprise first circuits 1 for measuring impedances at couplings 12 arranged to carry possibly dimmed feeding signals for the lamps 14. The first circuits 1 provide first output signals defining the measured impedances that comprise impedances at frequencies larger than mains frequencies. The detection circuits 1, 2 further comprise second circuits 2 for analyzing the first output signals. The second circuits 2 provide second output signals defining the operating dimmers being present or not. The impedance may be measured several times per time-interval. A change in the measured impedance of a certain minimum deviation or more within the time-interval may be indicative for the presence of an operating dimmer. The second circuits 2 may comprise filters 21, averaging circuits 22, threshold circuits 23, comparators 24 and controllers 25.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A detection circuit for detecting a presence of an operating dimmer arranged to dim a lamp, the detection circuit comprising:
   a first circuit configured to measure at one or more frequencies an impedance at a coupling arranged to carry a possibly dimmed feeding signal for the lamp and to provide a first output signal, the first output signal indicating the measured impedance at the one or more frequencies, the coupling being adapted to connect to a mains and the operating dimmer, and the one or more frequencies being higher than a mains frequency of the mains, and
   a second circuit configured to analyze the first output signal and to provide a second output signal, the second output signal indicating whether the operating dimmer is present,
   wherein the measured impedance comprises the impedance of the operating dimmer when the operating dimmer is present, and the second circuit is configured for providing the second output signal indicating the operating dimmer being present if the measured impedance changes by at least a defined minimum deviation within a defined time interval.

2. The detection circuit of claim 1, the first circuit being arranged to measure the impedance more than two times within the time-interval.

3. The detection circuit of claim 1, the second circuit comprising:
   a filter configured to filter the first output signal,
   an averaging circuit configured to average the filtered first output signal,
   a threshold circuit configured to provide at least a first threshold value in response to the averaged and filtered first output signal,
   a comparator configured to compare the filtered first output signal with the first threshold value, and
   a controller configured to produce the second output signal in response to a comparison result from the comparator.

4. The detection circuit of claim 3, the threshold circuit being further configured to provide a second threshold value, the comparator being further configured to compare the filtered first output signal with the second threshold value, and the controller being arranged to produce the second output signal in response the comparison by the comparator of the filtered first output signal with the first and second threshold values.

5. The detection circuit of claim 3, wherein the controller is arranged to produce the second output signal further in response to at least one of the first output signal, the filtered first output signal, and the averaged and filtered first output signal.

6. The detection circuit of claim 1, the first circuit comprising:
   a first input configured to be connected to said coupling,
   a second input configured to receive a signal at said one or more frequencies from an external generator, and
   an output for providing one of the first output signal or a filtered first output signal.

7. The detection circuit of claim 6, the first circuit further comprising:
   a transformer, a first winding being coupled to the first input, a second winding being coupled to the second input, the second winding further being coupled to a network, the network being coupled to the output.

8. A method for detecting a presence of an operating dimmer arranged to dim a lamp, the method comprising the steps of:
   measuring at one or more frequencies an impedance at a coupling arranged to carry a possibly dimmed feeding signal for the lamp, and providing a measurement result, the coupling being adapted to connect to a mains and the operating dimmer, the one or more frequencies being greater than a mains frequency of the mains, the measurement result indicating the measured impedance at the one or more frequencies higher than the mains frequency, and
   analyzing the measurement result and providing an analysis result, the analysis result indicating whether the operating dimmer is present, wherein the analysis result indicates the operating dimmer being present if the measured impedance at the one or more frequencies changes by at least a defined minimum deviation within a defined time interval.

9. The method of claim 8, wherein measuring the impedance at the coupling at the one or more frequencies comprises measuring the impedance at the one or more frequencies more than two times within the time-interval.

10. The method of claim 8, wherein analyzing the measurement result and providing the analysis result comprises:
    filtering the measurement result;
    averaging the filtered measurement result;
    providing at least a first threshold value in response to the averaged and filtered measurement result;
    comparing the filtered measurement result with the first threshold value, and
    producing the analysis result in response to a comparison result from the comparator.

11. The method of claim 10, further comprising:
    providing a second threshold value;
    comparing the filtered measurement result with the second threshold value; and
    producing the analysis result in response to the comparison by the comparator of the filtered measurement result with the first and second threshold values.

12. The method of claim 8, wherein measuring at the one or more frequencies an impedance at the coupling arranged to carry the possibly dimmed feeding signal for the lamp includes adding to the coupling a signal at the one or more frequencies, and measuring the impedance at the one or more frequencies in response to the added signal.

13. The method of claim 8, wherein the signal at the one or more frequencies is added to the coupling by a switching power converter, and wherein a filter is coupled between the switching power converter and the mains, the method further comprising adjusting a switching frequency of the switching power converter from a first frequency where the filter has a first attenuation to a second frequency where the filter has a second attenuation which is less than the first attenuation, wherein the one of more frequencies is the switching frequency.

14. An apparatus, comprising:
   a first circuit configured to measure at one or more frequencies an impedance at a coupling which is configured to carry a periodic signal from a first unit for powering a lamp, the first circuit being further configured to provide a first output signal indicating the measured impedance at the one or more frequencies, the one or more frequencies being higher than a frequency of the periodic signal, wherein the first circuit is configured to measure the impedance a plurality of times within a period of the periodic signal, and a second circuit configured to receive the first output signal and in response thereto to provide a second output signal indicating whether the first unit includes an operating dimmer, wherein the measured impedance comprises the impedance of the operating dimmer when the operating dimmer is present, and wherein the second circuit is configured for providing the second output signal indicating the operating dimmer being present if the measured impedance changes by at least a defined minimum deviation within a period of the periodic signal.

15. The apparatus of claim 14, wherein the second circuit includes: the second circuit comprising:

a filter configured to filter the first output signal, an averaging circuit configured to average the filtered first output signal, a threshold circuit configured to provide at least a first threshold value in response to the averaged and filtered first output signal, a comparator configured to compare the filtered first output signal with the first threshold value, and a controller configured to produce the second output signal in response to a comparison result from the comparator.

16. The apparatus of claim 15, the threshold circuit being further configured to provide a second threshold value, the comparator being further configured to compare the filtered first output signal with the second threshold value, and the controller being arranged to produce the second output signal in response to the comparison by the comparator of the filtered first output signal with the first and second threshold values.

17. The apparatus of claim 14, further comprising:

a switching power converter connected between the coupling and the lamp; and a filter is coupled between the switching power converter and the mains, wherein the apparatus is configured to adjust a switching frequency of the switching power converter from a first frequency where the second filter has a first attenuation to a second frequency where the second filter has a second attenuation which is less than the first attenuation, and wherein the one of more frequencies is the switching frequency.

18. The apparatus of claim 14, further comprising a generator configured to generate a signal at the one or more frequencies, and wherein the first circuit is configured to provide the generated signal to the coupling and to measure the impedance at the one or more frequencies in response to the generated signal.

19. The apparatus of claim 14, further comprising the lamp.

* * * * *